US009782499B2

(12) United States Patent
Won et al.

(10) Patent No.: US 9,782,499 B2
(45) Date of Patent: Oct. 10, 2017

(54) BLOCK COPOLYMER (BCP) ENCAPSULATED NANOPARTICLES AND METHODS OF USE THEREOF

(71) Applicant: Purdue Research Foundation, West Lafayette, IN (US)

(72) Inventors: You-Yeon Won, West Lafayette, IN (US); Ronald P. Andres, West Lafayette, IN (US); Dae Hwan Kim, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 767 days.

(21) Appl. No.: 13/837,705

(22) Filed: Mar. 15, 2013

(65) Prior Publication Data

US 2013/0261710 A1     Oct. 3, 2013

Related U.S. Application Data

(60) Provisional application No. 61/619,548, filed on Apr. 3, 2012.

(51) Int. Cl.
| | | |
|---|---|---|
| *A61K 9/00* | (2006.01) | |
| *A61K 49/18* | (2006.01) | |
| *A61N 5/00* | (2006.01) | |
| *A61N 5/04* | (2006.01) | |
| *A61K 41/00* | (2006.01) | |

(52) U.S. Cl.
CPC ...... *A61K 49/1857* (2013.01); *A61K 41/0052* (2013.01); *A61N 5/00* (2013.01); *A61N 5/04* (2013.01)

(58) Field of Classification Search
CPC .................................................. A61K 49/1857
See application file for complete search history.

(56) References Cited

U.S. PATENT DOCUMENTS

| | | | |
|---|---|---|---|
| 7,186,398 B2 | 3/2007 | Andres et al. | |
| 2002/0072069 A1* | 6/2002 | Ford | B82Y 5/00 435/6.11 |
| 2005/0136258 A1* | 6/2005 | Nie | A61K 47/48861 428/402 |
| 2013/0011339 A1* | 1/2013 | Colvin | A61K 49/0019 424/9.321 |
| 2014/0023715 A1* | 1/2014 | Yang | A61K 47/48861 424/491 |

FOREIGN PATENT DOCUMENTS

| | | | | |
|---|---|---|---|---|
| CN | 102294040 A | * | 12/2011 | |
| DE | WO 2010012372 A1 | * | 2/2010 | ............ B01F 17/005 |

OTHER PUBLICATIONS

Machine translation of CN 102294040 A, Oct. 2015.*

(Continued)

*Primary Examiner* — Paul Dickinson
(74) *Attorney, Agent, or Firm* — Mark S. Cohen; Pearl Cohen Zedek Latzer Baratz LLP

(57) ABSTRACT

This invention provides block copolymer (BCP) encapsulated nanoparticles. The BCP-encapsulated nanoparticles are used in methods for targeting a tumor, in methods of imaging a tumor and in methods of treating cancer including hyperthermia of tumors. This invention further provides processes for preparation of BCP-encapsulated nanoparticles.

15 Claims, 12 Drawing Sheets

(56) References Cited

OTHER PUBLICATIONS

Machine translation of WO 2010012372 A1, Oct. 2015.*
Gary et al. "Influence of Nano-Carrier Architecture on in Vitro siRNA Delivery Performance and in Vivo Biodistribution: Polyplexes vs Micelleplexes", *ACS Nano* 2011, 5(5), 3493-3505.
Moran, et al. "Size-Dependent Joule Heating of Gold Nanoparticles Using Capacitively Coupled Radiofrequency Fields", *Nano Research*, 2009, 2(5), 400-405.
Nikoobakht et al. "Preparation and Growth Mechanism of Gold Nanorods (NRs) Using Seed-Mediated Growth Method", *Chem Mater*. 2003, 15(10), 1957-1962.
Sharma et al. "Effects of the Incorporation of a Hydrophobic Middle Block into a PEG-Polycation Diblock Copolymer on the Physicochemical and Cell Interaction Properties of the Polymer-DNA Complexes", *Biomacromolecules* 2008, 9(11), 3294-3307.
Sharma et al. "Inhibitive Chain Transfer to Ligand in the ATRP of n-Butyl Acrylate", *Macromolecules* 2006, 39(14), 4680-4689.

* cited by examiner $t = 0$ $t = \sim 3$ months $t = \sim 6$ months $t = 0$ $t = 1$ day $t = 2$ days

BLOCK COPOLYMER (BCP) ENCAPSULATED NANOPARTICLES AND METHODS OF USE THEREOF

CROSS REFERENCE TO RELATED APPLICATIONS

This application claims the benefit of U.S. Provisional Application Ser. No. 61/619,548, filed on Apr. 3, 2012, which is incorporated herein by reference in its entirety.

GOVERNMENT INTEREST STATEMENT

This invention was made with government support under DMR0906567 awarded by the National Science Foundation. The government has certain rights in the invention.

FIELD OF THE INVENTION

This invention is directed toward block copolymer (BCP) encapsulated nanoparticles and to methods of use thereof for targeting and imaging tumors and for treating cancer.

BACKGROUND OF THE INVENTION

Cancer is currently the second leading cause of death in the U.S. (only next to heart disease). A new promising area of advances in cancer treatment is the application of excess heat to cancerous tissue called "hyperthermia" therapy. In particular, nanoparticle-mediated hyperthermia offers hope for treating cancer with no side effects by selective thermal ablation of the cancer cells. For this purpose, several nanoparticle materials have been proposed that can transduce near infrared light or magnetic energy into heat. However, these approaches have limitations that make them unsuitable for real clinical usage.

Nanoparticle-enhanced imaging and thermal destruction of tumors has been demonstrated using near infrared light to illuminate and heat gold nanoshells and gold nanorods. Although this method shows promise for treating cancer, it is only effective for treating sub-surface cancers (less than a few mm deep) because of the scattering and attenuation of near infrared light by biological tissues.

Magnetic nanoparticles have long been proposed as agents for non-invasive imaging and inductive hyperthermal destruction of cancer. If magnetic particles can be targeted to cancer tissue, they serve as effective contrast agents for MRI detection of a tumor. This is due to the fact that magnetic nanoparticles enhance the $T_2$ spin relaxation of water protons while leaving the $T_1$ relaxation largely undisturbed and this difference can be used to greatly enhance MRI contrast. Magnetic field-based hyperthermia is also a potentially effective method for treating deep tissue cancer, but it suffers from the limited heating potential of the magnetic particles that are currently available. The highest reported thermal power dissipation factor using iron oxide particles is a relatively low ~0.5 kW/g of particles. A further problem is that many magnetic particles lack long term magnetic stability and tend to aggregate in high electrolyte aqueous environments.

Recently, it has been discovered that Au nanoparticles can be heated remotely using a capacitively coupled radiofrequency (RF) field. If these particles can be targeted to a tumor, this RF heating can serve as an effective method for thermal destruction of deep tissue cancers. Curley and coworkers have heated Au nanoparticles using an RF field of 13.56 MHz, with diameters <50 nm at low ppm concentrations in water (Moran, et al, *Nano Research*, 2009, 2(5), 400-405). They report a high thermal power dissipation factor of ~380 kW/g of Au. However, this capacitive heating approach carries a high risk of uncontrolled heat production in the body because of the finite electrical conductivities of the human tissues and their heterogeneities.

SUMMARY OF THE INVENTION

In one embodiment this invention provides a block copolymer (BCP) encapsulated metallic nanoparticle, wherein said block-copolymer is amphiphilic. In one embodiment, the nanoparticle comprises Au. In one embodiment, the nanoparticle comprises Fe/Au.

In one embodiment this invention provides a method of tumor targeting, said method comprising:
  administering to a subject a composition comprising BCP-encapsulated metallic nanoparticles; and
  allowing said nanoparticles to reach and to adhere to a tumor.

In one embodiment this invention provides a method of tumor imaging, said method comprising:
  administering to a subject a composition comprising BCP-encapsulated metallic nanoparticles;
  allowing said nanoparticles to reach and to adhere to a tumor;
  imaging said subject;
wherein said imaging results in an image and wherein said image exhibits said adhered nanoparticles, thereby indicating the location of said tumor.

In one embodiment the imaging method is magnetic resonance imaging (MRI).

In one embodiment this invention provides a method of treating cancer, said method comprising:
  administering to a subject a composition comprising BCP-encapsulated metallic nanoparticles;
  allowing said nanoparticles to reach and to adhere to a tumor;
  optionally imaging said subject, wherein said imaging results in an image and wherein said image exhibits said adhered nanoparticles, thereby indicating the location of said tumor;
  applying electromagnetic radiation, a magnetic field or a combination thereof to said subject wherein said radiation/field produces heating of said nanoparticles resulting in heating of said tumor.

In one embodiment the electromagnetic radiation is applied in conjunction with the application of a magnetic field.

In one embodiment this invention provides a process for preparing a block copolymer(BCP)-encapsulated nanoparticles, said process comprising:
  dispersing a solution comprising surfactant-stabilized nanoparticles in a water/DMF mixture;
  preparing a DMF solution of a block copolymer (BCP);
  mixing said DMF solution of said block copolymer with said dispersion of nanoparticles to form a BCP-nanoparticles mixture;
  optionally sonicating said BCP-nanoparticles mixture;
  optionally adding water to said BCP-nanoparticles mixture, wherein said water addition is followed by sonication; and
  purifying said BCP-nanoparticles mixture.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
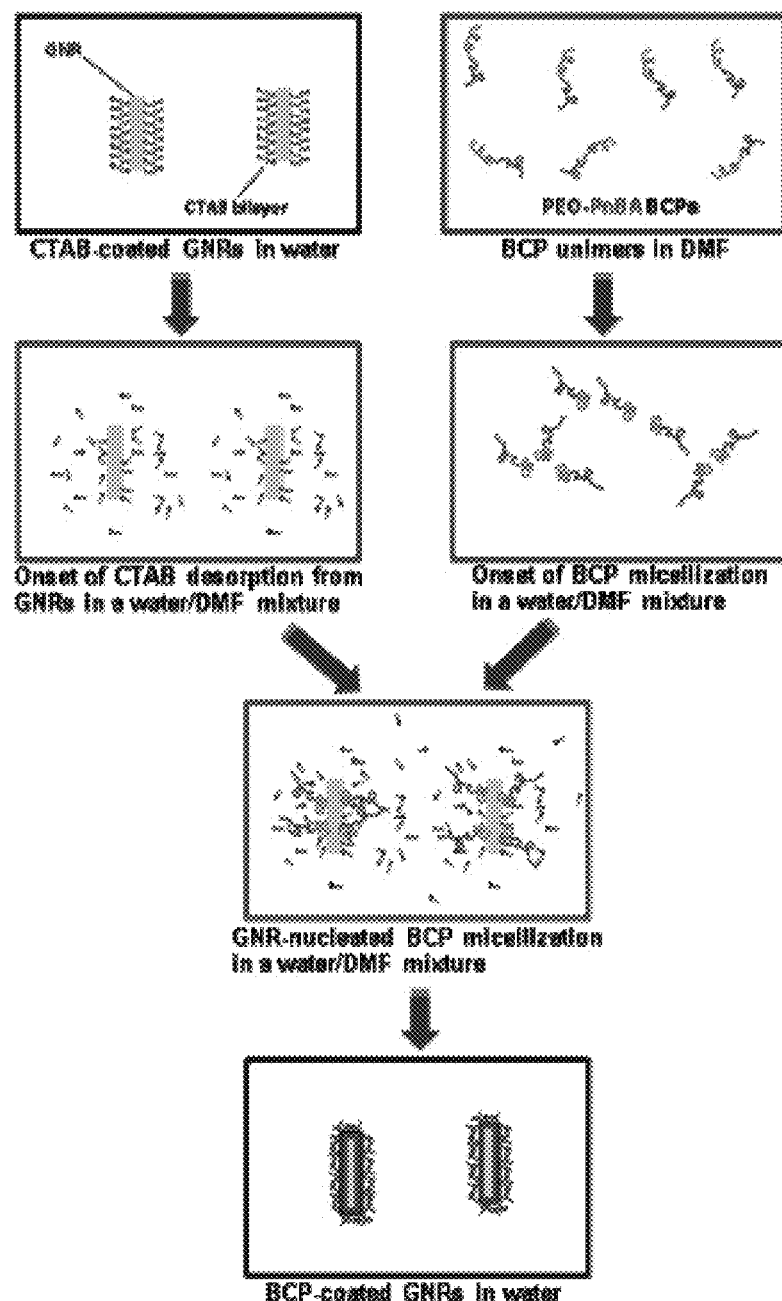
FIG. 1 depicts a schematic process for the preparation of block copolymers (BCP)-encapsulated gold nanorods (GNRs).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Polymer-Encapsulated Nanoparticles of the Invention

In one embodiment, this invention provides a block copolymer (BCP) encapsulated metallic nanoparticle wherein said block-copolymer is amphiphilic.

In one embodiment, the metallic nanoparticles of this invention are encapsulated within block copolymers. In one embodiment, the nanoparticles of the invention are Fe/Au nanoparticles. In another embodiment, the nanoparticles of this invention are gold nanorods (GNRs).

In one embodiment, the metallic nanoparticle is the core and the BCP is the shell of the BCP-encapsulated metallic nanoparticle. In one embodiment, the BCP is adhered to the surface of the nanoparticle. In one embodiment, the BCP forms a layer surrounding the nanoparticle. In one embodiment, the BCP forms a micelle within which the nanoparticle resides. In another embodiment, the BCP encapsulates a single nanoparticle.

Metallic Nanoparticles of the Invention

In one embodiment, the nanoparticles of the invention comprise Ag, Pd, Pt, Cu, Cr, Fe, Gd, Mn, Ni, Au, CdSe, GaAs, GaN, InAs, InN, oxides thereof, alloys thereof or a combination thereof. In one embodiment, the nanoparticle comprises Au. In one embodiment, the nanoparticle comprises Fe/Au.

In one embodiment, the atomic % of the Au in said Fe/Au nanoparticle is about 50% and wherein the atomic percent of said Fe is about 50% such that the Fe atom/Au atom ratio, is about 1:1, i.e., Fe(50%)/Au(50%). In one embodiment, the atoms of the Au and the atoms of the Fe are homogeneously distributed within said nanoparticle. In one embodiment, the nanoparticle is a superparamagnetic nanoparticle comprising Fe atoms and Au atoms distributed in a solid solution with no observable segregation into Fe-rich or Au-rich phases or regions.

In one embodiment, the metallic nanoparticle (NP) comprises one metal. In one embodiment, the nanoparticle comprises two or more metals. In one embodiment, the NP comprises a metal alloy. In one embodiment, in a nanoparticle comprising two or more metals, the metals are homogenously distributed in the NP. In one embodiment, the NP comprises a core and a shell (i.e., a core-shell particle). In one embodiment, the metal composition of the core is different from the metal composition of the shell. In one embodiment, the core comprises one metal and the shell comprises another metal. In one embodiment, the core comprises two or more metals wherein at least one of these metals is not present in the shell. In one embodiment, the shell comprises two or more metals wherein at least one of these metals is not present in the core.

In one embodiment, the nanoparticle is equiaxed with spherical morphology. In one embodiment, the nanoparticle is spherical. In one embodiment, the nanoparticle is rod shaped. In one embodiment, the NP is elliptical, oval, triangular, or cubical or comprises five or more faces or sides. In one embodiment, the NP is a hexahedron, or any other polyhedron. In one embodiment, the NP is cylindrical or conical. In one embodiment, the NP is symmetric. In one embodiment, the NP is of a non-symmetric or partially-symmetric geometry. In one embodiment, the surface of the NP is smooth. In one embodiment, the surface of the NP is ragged.

In one embodiment, the diameter of said nanoparticle excluding the BCP layer is ranging between about 1 nm to about 50 nm or between about 10 nm to about 50 nm or between about 1 nm to about 100 nm or between about 1 nm to about 25 nm or between about 25 nm to about 75 nm or between about 5 nm to about 20 nm or between about 50 nm to about 100 nm For a non-symmetric or partially symmetric NP, the largest dimension defining the particle is within the range described herein above for the diameter of a spherical particle. For example, the largest dimension for a rod-shaped particle is the length of the particle. For a non-symmetric particle, the largest dimension is the longest distance between two points on the surface of the particle.

In one embodiment, the length of said nanoparticle excluding the BCP layer is ranging between about 5 nm to about 50 nm. In one embodiment, the length of said nanoparticle excluding the BCP layer is ranging between about 2 nm to about 75 nm. In one embodiment, the average dimensions of a rod-shaped NP excluding the BCP layer are 18 nm (cross-sectional diameter) by 50 nm (length).

In one embodiment, the nanoparticle is characterized by a uniform volume magnetization. In one embodiment, the nanoparticle is Fe/Au and has a saturation magnetization proportional to the number of Fe atoms in the nanoparticle. In one embodiment, the Fe atoms in the interior of the nanoparticle are protected from oxidation. In one embodiment, the NP is superparamagnetic. In one embodiment, in the presence of magnetic field, the particle has significant resonant absorption at the microwave range of the to electromagnetic radiation spectrum. In one embodiment, in the presence of magnetic field, the particle has significant resonant absorption at the radiofrequency range of the electromagnetic radiation spectrum.

Polymers of the Invention

In one embodiment, the bock copolymers (BCP) of the invention comprise two polymeric chains attached to each other at one end. Linear block copolymers comprise two or more polymer chains in sequence, whereas a starblock copolymer comprises more than two linear block copolymers attached at a common branch point.

Block copolymers are useful in many applications where a number of different polymers are connected together to yield a material with hybrid properties. Attachment of a water soluble polymer to a water insoluble polymer forms an amphiphilic copolymer that may form micelles in solution. The BCP of this invention is an amphiphilic BCP.

In one embodiment, the BCP is described as a polymeric chain comprises "A" units (monomers) and "B" units (monomers). In one embodiment, the BCP is described as AAAA-BBBB polymeric chain or as $(A)_n$-$(B)_m$ chain wherein "n" and "m" represent the number of monomers in each chain while "A" and "B" represent the monomers. In one embodiment, the BCP is described as comprising two polymers. In another embodiment, the BCP of this invention is nonionic. In another embodiment, one component polymer (e.g. polymer A) of the BCP of this invention is ionic. In another embodiment, the BCP of this invention is amphiphilic. In one embodiment, the BCP comprises polymer A and polymer B, attached to each other at one end. In one embodiment, polymer A or polymer B comprises poly(acrylic acid), poly(methacrylic acid), poly(vinyl sulfonic acid), poly(vinyl benzyl trimethyl ammonium chloride), poly(acrylamidopropyl trimethyl ammonium chloride), poly(ethylene oxide) (poly(ethylene glycol)), poly(propylene oxide) (poly(propylene glycol)), poly(butyl acrylate), poly(methyl acrylate), poly(ethyl acrylate), poly(methyl methacrylate), polystyrene, carboxymethyl cellulose, dextran, poly(vinyl alcohol), polyvinylpyrrolidone, polyproline, poly(lactic acid), poly(glycolic acid), polycaprolactone, polyethylenimine, poly(2-(dimethylamino)ethyl methacrylate), polylysine, poly(methyl oxazoline), poly(ethyl oxazoline), or any combination thereof.

In one embodiment, polymer A, B or a combination thereof are chosen such as to exhibit substantially longer half-lives in blood following intravenous injection. Such to polymers may also increase the compound's solubility in aqueous solution, eliminate aggregation, enhance the physical and chemical stability of the NP and greatly reduce the immunogenicity of the NP. As a result, the desired in vivo biological activity may be achieved by the administration of such polymer-encapsulated NPs.

In one embodiment, the BCP comprises poly(ethylene oxide)-poly(n-butyl acrylate) (PEO-PnBA). In another embodiment, the BCP is $PEO_{113}$-$PnBA_{57}$. In another embodiment, the BCP is $PEO_{113}$-$PnBA_{89}$. In one embodiment, the BCP is linked to the surface of said nanoparticle. In one embodiment, BCP comprises a hydrophobic part and a hydrophilic part. In one embodiment, the hydrophilic part is selected so as to render the nanoparticle soluble in an aqueous solution. In one embodiment, the hydrophobic part is selected so as to enable bonding between said hydrophobic part of said BCP and said nanoparticle. In one embodiment, the PnBA (hydrophobic) part of the BCP is attached to the NP and the PEO (hydrophilic) part is exposed to the environment.

In one embodiment, the BCP-encapsulated nanoparticle comprising a plurality of targeting agents linked to said hydrophilic part. In one embodiment, the targeting agents are selected from the group consisting of a nucleic acid, a protein, a peptide, a carbohydrate and a lipid. In one embodiment, the role of the targeting agent is to bind to a tumor, e.g., by binding to a receptor that is present on the surface of the tumor. In one embodiment, targeting agents provides selective binding, i.e., they bind to a receptor that is over-expressed on a tumor cell surface relative to a normal/healthy cell surface. In another embodiment, non limiting examples of a targeting agent include an antibody, an antibody fragment, Protein A, Protein G, biotin, avidin, streptavidin, a metal ion chelate, an enzyme cofactor, a nucleic acid, a ligand, a receptor, an aptamer, or a lectin.

In one embodiment, in the BCP-encapsulated nanoparticle, the BCP layer is of a thickness ranging between 3 nm and 12 nm. In one embodiment, the BCP layer is of a thickness ranging between 1 nm and 5 nm or ranging between 5 nm and 15 nm or ranging between 5 nm and 10 nm or ranging between 2.5 nm and 7.5 nm or ranging between 4 nm and 60 nm or ranging between 4 nm and 20 nm. In one embodiment, the BCP layer is of a thickness of 7.3±1.2 nm In one embodiment, polymer A, polymer B or a combination thereof are hydrophilic. In one embodiment, polymer A is hydrophobic and polymer B is hydrophilic. In one embodiment, the hydrophilicity level of polymers A and B is designed so that polymer A will bind to the surface of the NP while polymer B will provide solubility in aqueous solutions and in the blood stream. In one embodiment, polymers A and B are non-toxic. In one embodiment, polymers A, B or a combination thereof are biocompatible and/or biodegradable. In another embodiment, polymer A, polymer B or combination thereof are nonionic. In another embodiment, polymer A or polymer B is ionic.

Methods of the Invention

In one embodiment, this invention provides a method of tumor targeting, said method comprising:
   administering to a subject a composition comprising BCP-encapsulated metallic nanoparticles; and
   allowing said nanoparticles to reach and to adhere to a tumor.

In one embodiment, this invention provides a method of tumor imaging, said method comprising:
   administering to a subject a composition comprising BCP-encapsulated metallic nanoparticles;
   allowing said nanoparticles to reach and to adhere to a tumor;
   imaging said subject;
   wherein said imaging results in an image and wherein said image exhibits said adhered nanoparticles, thereby indicating the location of said tumor.

In one embodiment, the imaging method is magnetic resonance imaging (MRI).

In one embodiment, this invention provides a method of treating cancer, said method comprising:
   administering to a subject a composition comprising BCP-encapsulated metallic nanoparticles;
   allowing said nanoparticles to reach and to adhere to a tumor;
   optionally imaging said subject, wherein said imaging results in an image and wherein said image exhibits said adhered nanoparticles, thereby indicating the location of said tumor;
   applying electromagnetic radiation, a magnetic field or a combination thereof to said subject wherein said radiation/field produces heating of said nanoparticles resulting in heating of said tumor.

In one embodiment, the electromagnetic radiation is applied in conjunction with the application of a magnetic field.

In one embodiment, the optional imaging step and said radiation/magnetic field application step is/are carried out in an MRI, EPR or ESR instrument.

In one embodiment, the step of applying electromagnetic radiation, a magnetic field or a combination thereof is conducted as follows: applying a magnetic field to a subject resulting in splitting of the spins of the unpaired electrons of the NP metal; exposing the subject (or areas thereof) to microwave (or RF) radiation that is absorbed by said NP as a result of the spin splitting Electron Paramagnetic Resonance (EPR) or electron spin resonance (ESR) involves excitation of electron spins under a magnetic field. The spins are excited using microwave radiation of a certain wavelength. For free unpaired electrons, in the presence of an external magnetic field, the electron's magnetic moment aligns itself either parallel or antiparallel to the field, each alignment having a specific energy. There is an energy separation between the lower and the upper spin states. The splitting of the energy levels is directly proportional to the magnetic fields strength. An unpaired electron can move between the two energy levels by either absorbing or emitting energy such that the resonance condition is obeyed. For different magnetic fields, the energy separation is different and therefore, the excitation energy varies with the field's strength.

Usually, EPR measurements are made with microwaves in the 9000-10000 MHz (9-10 GHz) region, with fields corresponding to about 3500 G (0.35 T). EPR spectra can be generated by either varying the photon frequency incident on a sample while holding the magnetic field constant or vice versa.

In one embodiment, this invention provides a theranostics (therapy and diagnostic) methods for treating cancer or other non-cancerous tumors. In one embodiment, methods of this invention rely on heat dissipation from excited spin states in a nanoparticle that is adhered to a tumor. According to this aspect and in one embodiment, BCP-coated NPs are adhered to a tumor. The NPs are then placed in a magnetic field causing splitting of spin levels in the NP. The NPs are irradiated by microwave radiation (or RF) in an energy corresponding to the energy difference between the two spin levels. The NP thus absorbs the microwave radiation (or RF). The NP emits the absorbed energy in the form of heat and this causes heating of the adjacent tumor. The tumor is then destructed, destroyed, blocked and/or to loses its functionalities.

The microwave (or RF) irradiating step can be preceded by a diagnostic step wherein the tumor, the NPs and their surroundings are imaged by ESR or by MRI. Advantages of methods of this invention include but are not limited to: i. large penetration depth of the microwaves (or RF) which allows destruction of tumors in deep tissue; ii. inductive heating of the NPs which prevents heating of other non-tumor tissues or body regions; iii. the ability to diagnose and treat the tumor in the same set-up and at the same time (e.g., diagnosis followed by immediate treatment);

In one embodiment, the heating of said tumor results in destruction of said tumor.

In one embodiment, the electromagnetic radiation is in the microwave range, the radiofrequency (RF) range or a combination thereof.

In one embodiment, the heating of said nanoparticles is an inductive heating process.

In one embodiment, the subject is exposed to low levels of said radiation so that other non-tumor tissues or body regions are not damaged.

In one embodiment, the tumor is in deep tissue. In one embodiment, the deep tissue is at a distance ranging between 2 cm and 4 cm or ranging between 2 cm and 6 cm or ranging between 1 cm and 5 cm from an external surface of the body of said subject. In another embodiment, the tumor is a non deep tissue. In another embodiment, the methods of this invention destruct tumors in tissues below 1.0 cm depth from the surface of the skin. In another embodiment, the methods of this invention destruct tumors in tissues ranging between 0 cm and 6 cm from an external surface of the body of said subject.

In one embodiment, the nanoparticles comprise Fe/Au. In one embodiment, the BCP-encapsulated nanoparticles have a resonant absorption of microwave radiation at frequencies ranging between 900 MHz and 3.0 GHz.

In one embodiment, the nanoparticles have a power dissipation factor ranging between $1\times10^3$ and $1\times10^8$ kW/g Fe.

In one embodiment, in a 0.32 Tesla magnet, the resonant microwave frequency of said Fe/Au nanoparticles is 9.3 GHz, and the power dissipation is about $8.1\times10^5$ kW/g Fe.

In one embodiment, in a 3-Tesla magnet, the resonant microwave frequency of said Fe/Au nanoparticles is 84 GHz, and the power dissipation is about $7.3\times10^6$ kW/g Fe.

In one embodiment, this invention uses polymer-passivated iron/gold (Fe/Au) alloy nanoparticles. The synthesis of this unique material is disclosed in U.S. Pat. No. 7,186,398 which is fully incorporated herein by reference. These nanoparticles have significant potential as agents capable of targeting tumor cells, of rendering these tumor cells visible by means of magnetic resonance imaging (MRI), and of facilitating non-invasive thermal destruction of the tumor cells.

Figure 11:
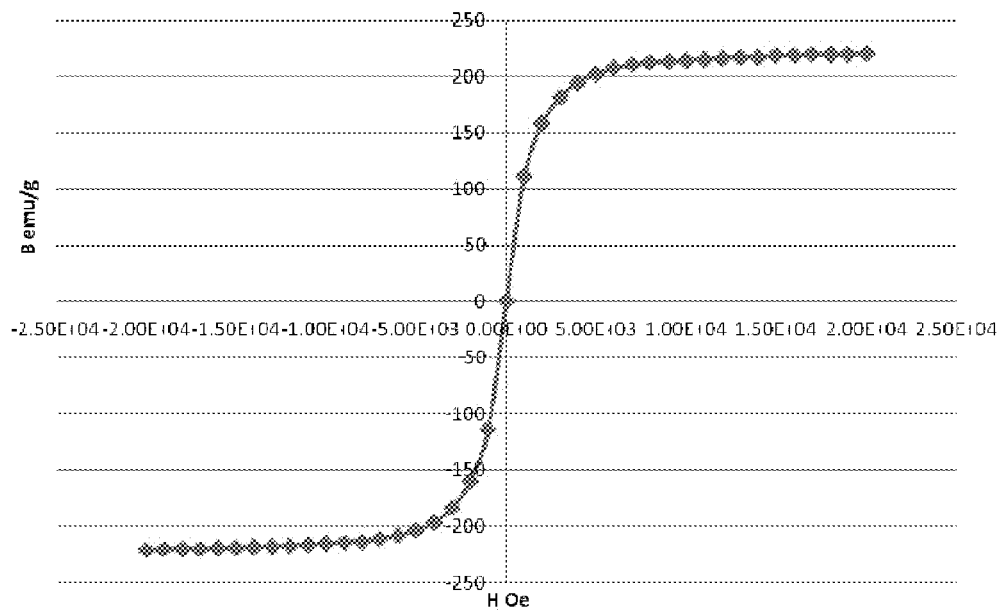
FIG. 11 depicts magnetization curves of a bulk sample of the 50/50 atomic % Fe/Au nanoparticles.
Figure 12:
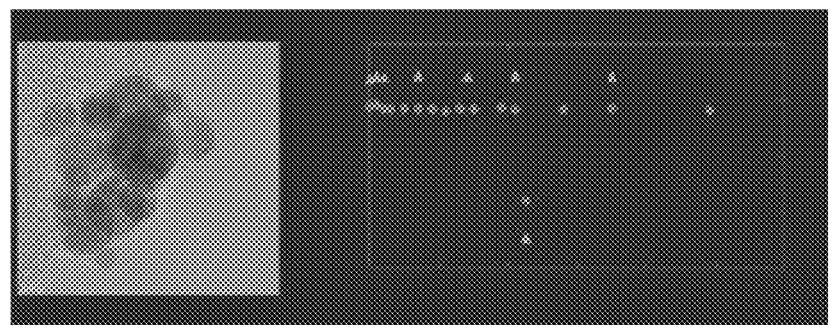
FIG. 12 (left) TEM micrograph and (right) hydrodynamic sizes of the block copolymer (BCP)-encapsulated Fe/Au nanoparticles.

In one embodiment, the BCP-encapsulated nanoparticle system is composed of a metallic Fe/Au nanoparticle core (synthesized by the aerosol reaction method) surrounded by an organic polymer monolayer (produced by a nanoparticle encapsulation method). The metal core is a metastable alloy consisting of Fe atoms homogeneously distributed in an Au matrix. This unique atomic structure give rise to superparamagnetic behavior at ambient conditions with a magnetic susceptibility value order of magnitude higher than that achievable with conventional iron oxide nanomaterials (FIGS. 11, 12). This material is an excellent candidate for use as a microwave heat transducer for tumor-selective hyperthermia.

The BCP-encapsulated nanoparticles of the invention provide efficient imaging agents. The BCP-encapsulated nanoparticles of the invention are used for targeted MRI/hyperthermia theranosis (i.e., therapy and diagnostics). The BCP-encapsulated nanoparticles of the invention can efficiently function as whole body MRI contrast agents. The BCP-encapsulated nanoparticles of the invention can be used as contrast agents for MRI of specific organs. The BCP-encapsulated nanoparticles of the invention are effective theranosis agents enabling non-invasive MRI identification and hyperthermia treatment of tumors.

In one embodiment, the adherence of said BCP-encapsulated nanoparticles to the tumor is achieved by linking a cell-targeting moiety to said BCP.

In one embodiment, the cell-targeting moiety adheres to said tumor upon contact with said tumor cells. In one embodiment, the cell-targeting moiety comprises folate.

In one embodiment, the BCP-coated NP further comprises a targeting moiety (i.e., a targeting agent). In one embodiment, the targeting agents are selected from the group consisting of a nucleic acid, a protein, a peptide, a carbohydrate and a lipid. In one embodiment, the role of the targeting agent is to bind to a tumor, e.g., by binding to a receptor that is present on the surface of the tumor. In another embodiment, non limiting examples of targeting agent include an antibody, an antibody fragment, Protein A, Protein G, biotin, avidin, streptavidin, a metal ion chelate, an enzyme cofactor, a nucleic acid, a ligand, a receptor, an aptamer, or a lectin.

In one embodiment, this invention provides a method of treating cancer. In another embodiment, this invention provides a method of treating benign tumors.

In another embodiment, the cancer comprises adrenocortical carcinoma, anal cancer, bladder cancer, brain tumor, brain stem glioma, brain tumor, cerebellar astrocytoma, cerebral astrocytoma, ependymoma, medulloblastoma, supratentorial primitive neuroectodermal, pineal tumors, hypothalamic glioma, breast cancer, carcinoid tumor, carcinoma, cervical cancer, colon cancer, endometrial cancer, esophageal cancer, extrahepatic bile duct cancer, ewings family of tumors (Pnet), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, kidney cancer, laryngeal cancer, leukemia, acute lymphoblastic, leukemia, oral cavity cancer, liver cancer, lung cancer, non small cell lung cancer, small cell lymphoma, AIDS-related lymphoma, central nervous system (primary) lymphoma, cutaneous T-cell lymphoma, Hodgkin's disease, non-Hodgkin's disease, malignant mesothelioma, melanoma, Merkel cell carcinoma, metastatic squamous carcinoma, multiple myeloma, plasma cell neoplasms, mycosis fungoides, myelodysplastic syndrome, myeloproliferative disorders, nasopharyngeal cancer, neuroblastoma, oropharyngeal cancer, osteosarcoma, ovarian epithelial cancer, ovarian germ cell tumor, ovarian low malignant potential tumor, pancreatic cancer, exocrine pancreatic cancer, islet cell carcinoma, paranasal sinus and nasal cavity cancer, parathyroid cancer, penile cancer, pheochromocytoma cancer, pituitary cancer, plasma cell neoplasm, prostate cancer, rhabdomyosarcoma, rectal cancer, renal cell cancer, salivary gland cancer, Sezary syndrome, skin cancer, spleen cancer, skin cancer, Kaposi's sarcoma, small intestine cancer, soft tissue sarcoma, testicular cancer, thymoma, malignant thyroid cancer, urethral cancer, uterine cancer, sarcoma, unusual cancer of childhood, vaginal cancer, vulvar cancer, Wilms' tumor, or any combination thereof.

The block copolymer (BCP)-stabilized metal nanoparticle material has resonant adsorption of microwave or of radio frequency (RF) radiation, and therefore provides a way to hyperthermally destroy cancer cells in deep tissue by low level exposure of the patient to microwave radiation tuned to the stationary magnetic field of the magnetic resonance imaging to (MRI) apparatus. At frequencies most commonly used for therapeutic applications (i.e., between 915 MHz and 2.45 GHz), the penetration depth of microwaves is in the range of about 2-4 cm.

The BCP-stabilized metal nanoparticles of this invention have a several orders of magnitude higher thermal power dissipation factor (close to ~$10^7$ kW/g Fe in one embodiment) while the inductive nature of the heating process of these nanoparticles makes it significantly safer for medical use.

Compositions and Methods of Administration

In one embodiment, the BCP-encapsulated nanoparticles or compositions comprising the BCP-encapsulated NP are administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment the BCP-coated NPs, are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In one embodiment, the compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In other embodiments, carriers or diluents are used in compositions comprising the BCP-encapsulated NPs of this invention. In one embodiment, carriers for liquid formulations comprising the BCP-encapsulated NPs are aqueous or non-aqueous solutions, suspensions, emulsions or oils.

In another embodiment, parenteral vehicles (for subcutaneous, intravenous, intraarterial, or intramuscular injection) are used for administering the BCP-coated NPs of the invention to a subject.

In other embodiments, the compositions comprising the BCP-coated NPs further comprise excipients, binders, disintegrating agents, buffers, additives such as albumin or gelatin to prevent absorption to surfaces, detergents, protease inhibitors, surfactants, permeation enhancers, solubilizing agents, anti-oxidants, stabilizers, viscosity increasing agents, sweeteners, preservatives, lubricants, flow-aids, plasticizers, emulsifiers, polymer coatings, coating and film forming agents and/or adjuvants. Each of the above additives, excipients, formulations and methods of administration represents a separate embodiment of the present invention.

Processes of the Invention

In one embodiment, this invention provides a process for preparing a block copolymer (BCP)-encapsulated nanoparticles, said method comprising:
dispersing a solution comprising surfactant-stabilized nanoparticles in a water/DMF mixture;
preparing a DMF solution of a block copolymer (BCP);
mixing said DMF solution of said block copolymer with said dispersion of nanoparticles to form a BCP-nanoparticles mixture;
optionally sonicating said BCP-nanoparticles mixture;
optionally adding water to said BCP-nanoparticles mixture, wherein said water addition is followed by sonication; and
purifying said BCP-nanoparticles mixture.

In one embodiment, the process for preparing a block copolymer (BCP)-encapsulated nanoparticles provides a step of dispersing a solution comprising surfactant-stabilized nanoparticles in a water/DMF mixture. In one embodiment, the nanoparticles are gold nanorods (GNRs). In one embodiment, the GNRs comprises average dimensions of about 18 nm (cross-sectional diameter) by 50 (length) nm. In one embodiment, the surfactant is CTAB. In one embodiment, the nanoparticles comprise Fe and Au (Fe/Au). In one embodiment, the nanoparticles are superparamagnetic. In one embodiment, the nanoparticles consist of Fe atoms and Au atoms, and wherein the Fe atom/Au atom ratio is about 1:1, i.e., Fe(50%)/Au(50%). In one embodiment, the magnetic moment of the nanoparticles is proportional to the number of Fe atoms in the nanoparticles.

In one embodiment, the Fe/Au nanoparticles are prepared by evaporating a metal comprising Fe atoms and Au atoms using an atmospheric pressure direct current arc discharge to yield a metal vapor; contacting said metal vapor with a forced convective flow of argon gas to control particle nucleation and growth, yielding solid metal nanoparticles such that the Fe atoms and the Au atoms are distributed in a solid solution with no observable segregation into Fe-rich or Au-rich phases or regions; contacting the nanoparticles with a forced convective flow of helium or nitrogen gas to yield cooled nanoparticles; and bubbling said cooled nanoparticles through a liquid to yield a colloidal suspension of superparamagnetic nanoparticles. In another embodiment, the liquid is aqueous sodium citrate. In another embodiment, the liquid is aqueous sodium carbonate. In another embodiment, the liquid is an organic solvent. In another embodiment, the liquid is mesitylene.

In one embodiment, the process for the preparation of the Fe/Au nanoparticles further comprises controlling the composition of the nanoparticles by controlling the loading ratio of Fe vs. Au atoms. In one embodiment, the process further comprises controlling the mean size of the particles by controlling the metal evaporation rate, the argon flow rate, or both. In one embodiment, the rate of production of nanoparticles is on the order of grams per hour. In one embodiment, the process further comprises linking a surfactant to the surface of said nanoparticles.

In one embodiment, the process for preparing a block copolymer (BCP)-encapsulated nanoparticles provides a step of preparing a DMF solution of a block copolymer. In another embodiment, the BCP comprises poly(ethylene oxide)-poly(n-butyl acrylate) (PEO-PnBA). In one embodiment, the monomer number of said PEO block ranges between 10 and 150. In one embodiment, the monomer number of said PnBA block ranges between 10 and 100. In one embodiment, the composition of said PEO-PnBA block copolymer ranges between 1:9 and 9:1 in PEO:PnBA weight ratio. In one embodiment, the PEO-PnBA comprises $PEO_{113}$-$PnBA_{57}$, $PEO_{113}$-$PnBA_{89}$ or a combination thereof. In one embodiment, the polydispersity indices of said copolymers are less than 1.2 for a ($PEO_{113}$-$PnBA_{89}$) and less than 1.2 for a ($PEO_{113}$-$PnBA_{57}$).

In one embodiment, the process for preparing a block copolymer (BCP)-encapsulated nanoparticles provides a step comprising mixing a DMF solution of the block copolymer with a dispersion of nanoparticles in a water/DMF mixture to form a BCP-nanoparticles mixture, wherein the $W_{water}$ (water weight fraction in the water/DMF mixture) in said mixture is between 0.01 and 0.99. In another embodiment the $W_{water}$ (water weight fraction in the water/DMF mixture) in said mixture is between 0.1 and 0.5. In another embodiment the $W_{water}$ (water weight fraction in the water/DMF mixture) in said mixture is between 0.3 and 0.4. In another embodiment the $W_{water}$ (water weight fraction in the water/DMF mixture) in said mixture is between 0.2 and 0.7. In another embodiment the $W_{water}$ (water weight fraction in the water/DMF mixture) in said mixture is between 0.05 and 0.5.

In one embodiment, the process for preparing a BCP-encapsulated nanoparticles of this invention includes a purifying step including purifying the BCP-nanoparticles mixture. In another embodiment, the purifying step is conducted by membrane dialysis, by centrifugation followed by re-suspension or combination thereof.

Definitions:

In one embodiment, BCP-stabilized nanoparticles are referring to BCP-encapsulated nanoparticles or to BCP-coated nanoparticles. BCP-stabilized nanoparticles are nanoparticles that are attached to BCP. The BCP is attached, bonded, adhered or interacts with the surface of the nanoparticles.

Attachment of the BCP provides for stabilization of the formed BCP-coated NP of this invention. In one embodiment, the term "stabilized" or "stabilization" refers to the stability of the resulting coated NPs in solution following their production. In one embodiment, the terms "stabilized" and "stabilization" refer to the fact that the coated NPs do not aggregate or "settle out" in solution. In another embodiment, the coated/encapsulated NPs do not change in their chemical composition over a particular period of time.

In one embodiment, nanoparticles are particles with at least one dimension ranging between 1 nm and 100 nm. In another embodiment, nanoparticles are particles with at least one dimension ranging between 1 nm and 1000 nm. In one embodiment, a nanopartiacle is termed NP and nanoparticles NPs.

In one embodiment, block copolymer (BCP) refers to two or more polymer chains attached at their ends. Linear block copolymers comprise two or more polymer chains in sequence, whereas a starblock copolymer comprises more than two linear block copolymers attached at a common branch point. Block copolymers are useful in many applications where a number of different polymers are connected together to yield a material with hybrid properties. Attachment of a water soluble polymer to a water insoluble polymer forms an amphiphilic copolymer that may form micelles in solution.

In one embodiment, hydrodynamic diameter is the effective diameter of a particle in a liquid environment. When a dispersed particle moves through a liquid medium, a thin electric dipole layer may adhere to its surface. Since this layer influences the movement of the particle, the dynamic light scattering (DLS) diameter measurement will yield a "hydrodynamic particle diameter" which is mostly above the diameter measured for example with a transmission electron microscope (TEM). The thickness of the electric dipole layer depends on various factors, such as the electrical conductivity of the liquid.

In one embodiment, high ionic strength means a solution in which the ionic strength is high. The ionic strength of a solution is a measure of the concentration of ions in that solution. Ionic compounds, when dissolved in water, dissociate into ions. The dissolved ions in solution will affect important properties such as the dissociation or the solubility of different salts and other compounds. The ionic strength of a solution is a function of the concentration of all ions present in that solution.

In one embodiment, superparamagnetic is a magnetic property found for example in particles of ferromagnetic materials such as iron oxide of a size below approximately 100 nm in diameter. Such particles, would, in theory, no longer exhibit the cooperative phenomenon of ferromagnetism found in the bulk, and instead, might be superparamagnetic, exhibiting strong paramagnetic properties with large susceptibility.

In one embodiment, a solid solution is a mixed crystal. A solid solution comprises a host crystal comprising a first constituent. The host crystal further comprises a second constituent which fits into and is distributed in the lattice of the host crystal.

In one embodiment, uniform volume magnetization refers to a state of magnetization to of a material wherein the magnetization is uniform throughout/within the body of the material.

In one embodiment, saturation magnetization is the maximal magnetization that is possible for a physical object under certain conditions.

In one embodiment, tumor targeting refers to the ability of a substance, a material, a particle, a polymer or of the BCP-coated NPs of the invention to identify a tumor and to adhere to a tumor. Tumor targeting refers to the selective binding or adhesion of the targeting agent to a tumor, while ideally no or little binding to non-tumor cells is observed.

In one embodiment, tumor imaging refers to the imaging of a tumor and usually imaging of the surroundings of the tumor. In methods of the invention, when the BCP-coated NPs selectively bind to a tumor, the NPs can be imaged and thus reveal, confirm or provide further evidence for the location of the tumor.

In one embodiment, inductive heating process refers to a heating process wherein the heat develops in the working piece that is electrically conductive (such as metal or semiconductor), and therefore there is no need for a transmission medium for producing heat.

In one embodiment, power dissipation factor refers to the value of the tendency of a dielectric material to absorb part of the energy when an AC field is applied.

In one embodiment, resonant microwave frequency at a certain magnetic field is the frequency that corresponds to the energy separation between the upper and lower spin states produced by an applied magnetic field.

In one embodiment, cell-targeting moiety is a cell-targeting agent. In one embodiment, the multi-polymer-coated magnetic nanocluster further comprises a targeting moiety. The term "targeting moiety", in one embodiment, refers to a specificity conferred to the moiety, which results in attachment of the moiety to a cognate partner, or, in another embodiment, an ability to specifically "target" the moiety to a desired cognate partner molecule. The targeting moiety may, in one embodiment, facilitate attachment of the multi-polymer-coated magnetic nanocluster, through the targeting moiety, to a protein or glycoprotein of interest, in one embodiment, or, in another embodiment, to a nucleic acid of interest, or in another embodiment, to a cellular fraction of interest or to any other receptor, molecule, or chemical compound residing on the surface of a tumor cell.

In one embodiment, the targeting moiety enhances attachment to a molecule in low abundance, which is of interest. In another embodiment, the targeting moiety enhances attachment following supply of an energy source, such as a UV light source. In one embodiment, the targeting moiety is chemically attached to the polymers via a chemical cross-linking group, or in another embodiment, forms a stable association with a polymer of the multi-polymer-coated magnetic nanocluster, or in another embodiment, forms an association with the polymer of the multi-polymer-coated magnetic nanocluster, which readily dissociates following changes in solution conditions, such as salt concentration or pH.

In one embodiment, the targeting moiety may be an antibody, which specifically recognizes a molecule of interest, such as a protein or nucleic acid. In another embodiment, the antibody may specifically recognize a reporter molecule attached to a molecule of interest. In another embodiment, the targeting moiety may be an antibody fragment, Protein A, Protein G, biotin, avidin, streptavidin, a metal ion chelate, an enzyme cofactor, or a nucleic acid. In another embodiment, the targeting moiety may be a receptor, which binds to a cognate ligand of interest, or associated with a cell or molecule of interest, or in another embodiment, the targeting moiety may be a ligand which is used to "fish out" a cell via interaction with its cognate receptor.

In one embodiment, the polydispersity index of a polymer is a measure of the spread of molecular weight distribution in the polymer, and is defined as the ratio of the ration of the weight-average molecular weight to the number-average molecular weight. [

In one embodiment, $W_{water}$ is the weight fraction of water in the water/DMF mixture. When the $W_{water}$ is 0.3 then the $W_{DMF}$ is 0.7. The process for preparing a block copolymer (BCP)-encapsulated nanoparticles provides a step comprising mixing a DMF solution of the block copolymer with a dispersion of nanoparticles in a DMP/water mixture to form a BCP-nanoparticles mixture, wherein the W water (water weight fraction) in said mixture is between 0.3-0.4.

EXAMPLES

Example 1

Preparation of PEO-PnBA Block Copolymer-Encapsulated Gold Nanorods

Figure 2:
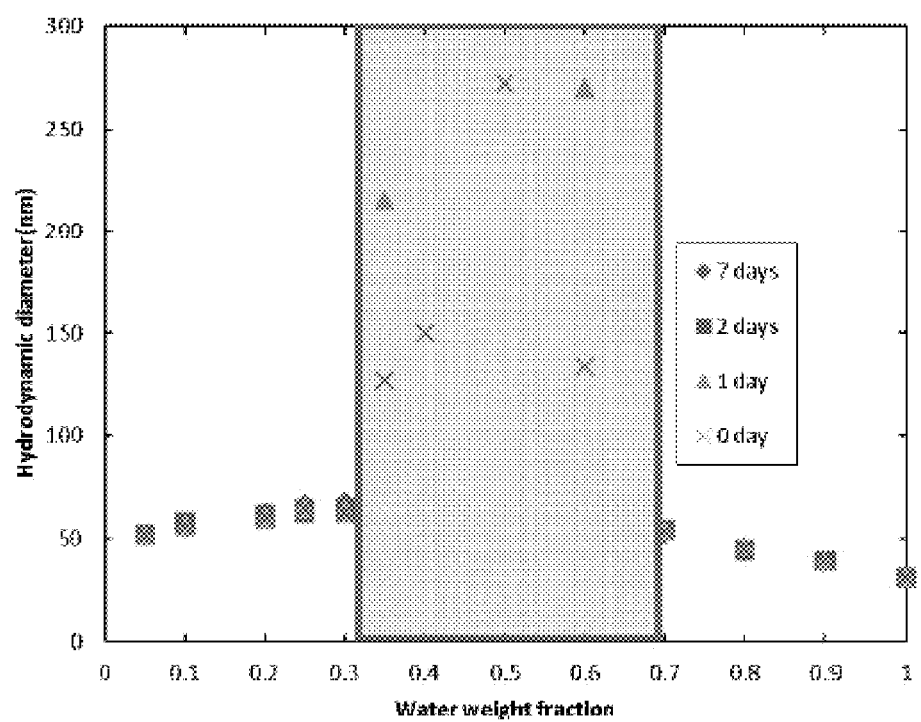
FIG. 2 presents mean hydrodynamic diameters (measured by dynamic light scattering DLS) of CTAB-stabilized GNRs in binary water/DMF mixtures as a function of $w_{water}$ and time. The shaded area represents the solvent composition window in which CTAB desorbs from GNRs.
Figure 5:
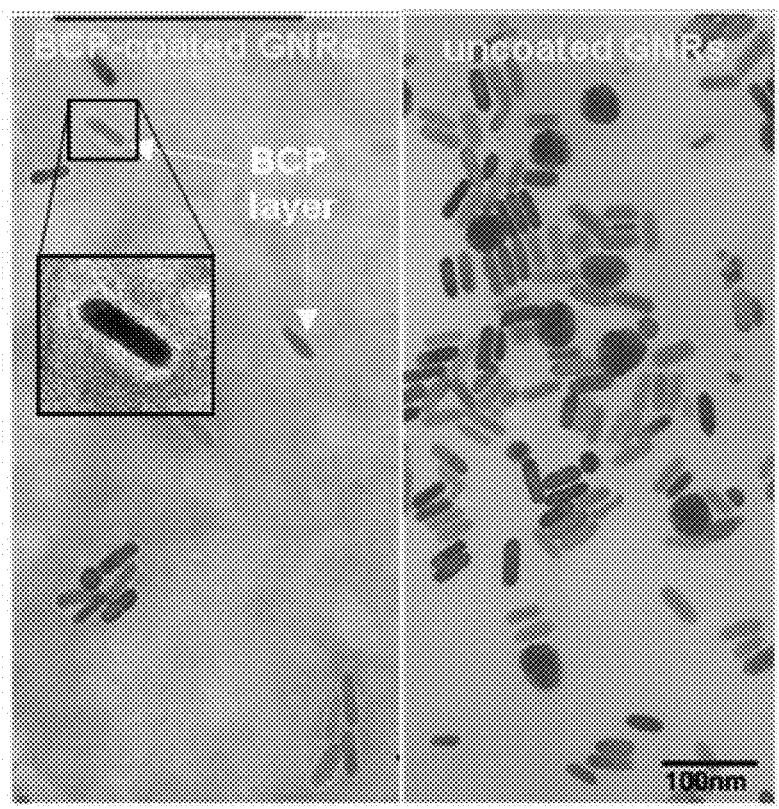
FIG. 5 depicts representative transmission electron microscopy (TEM) images of (left) $PEO_{113}$-$PnBA_{57}$ BCP-coated GNRs (prepared by surfactant exchange at a solvent composition of $w_{water}$=0.35, stored in pure water for 30 days after preparation) and (right) CTAB-coated GNRs (as synthesized in water), both negatively stained with (2%) uranyl acetate. Additional images of these samples are presented in FIGS. 9 and 10.

Materials. The $PEO_{113}$-$PnBA_{89}$ and $PEO_{113}$-$PnBA_{57}$ diblock copolymer samples were synthesized and characterized as described in previous publications: Sharma R. et al. *Macromolecules* 2006, 39(14), 4680-4689; Sharma R. et al. *Biomacromolecules* 2008, 9(11), 3294-3307; and Gary, D. J., et al. *ACS Nano* 2011, 5(5), 3493-3505 which are hereby incorporated by reference. The polydispersity indices of these copolymers were determined (by gel permeation chromatography (GPC)) to be 1.15 ($PEO_{113}$-$PnBA_{89}$) and 1.15 ($PEO_{113}$-$PnBA_{57}$). GNRs were synthesized using the procedure disclosed in Nikoobakht, B. et al., *Chem Mater.* 2003, 15(10), 1957-1962 which is hereby incorporated by reference. As shown in FIG. 5, the GNR particles used have an average dimension of about 18 nm (cross-sectional diameter) by 50 (length) nm Surfactant exchange procedure and encapsulation procedure. CTAB (Surfactant) was removed from the GNR surface just prior to their encapsulation with the BCP, as it compromises the affinity of the gold surface to the BCP. Dimethylformamide (DMF) was used as an organic co-solvent to control the partitioning of CTAB between the gold surface and the solution phase. When the DMF weight fraction ($w_{DMF}$) was above 0.30, CTAB desorbs from the gold surface and induces the aggregation of the uncoated GNR particles (FIG. 2). In the DMF-rich regime (when $w_{DMF}$ is above 0.70), the CTAB-coated GNRs were again stabilized and return to a well-dispersed state, because of the relatively poor solubility of the CTAB head group in the lower dielectric solvent mixture. In another embodiment, the GNRs may be encased in reverse micelles of CTAB.

A solution of cetyl trimethylammonium bromide (CTAB)-stabilized GNRs (0.01 mg/ml) was initially dispersed in a water/DMF mixture with $w_{water}$=0.70. A DMF solution of $PEO_{113}$-$PnBA_{57}$ (1.0 mg/ml) was prepared separately, then mixed in equal amounts with the GNR solution (each 1.0 ml) so that the final solvent composition contained a water weight fraction of 0.35. The mixture was sonicated for 30 minutes in a sonicating bath, then characterized by DLS. The mean hydrodynamic diameter of the (presumably BCP-encapsulated) GNR particles was determined be about 85 nm Water (0.6 ml) was added to a final solvent composition of $w_{water}$=0.50, followed by another 30 minutes of sonication. This reduced the hydrodynamic diameter of the GNRs to about 75 nm, which suggests that the BCP coating became more compact under more polar solvent conditions. The GNR suspension was then purified by membrane dialysis (molecular weight cutoff 3,000) for 2 days against a large volume of deionized water to remove residual DMF and CTAB; 2.6 ml of the final GNR solution was obtained.

Figure 6:
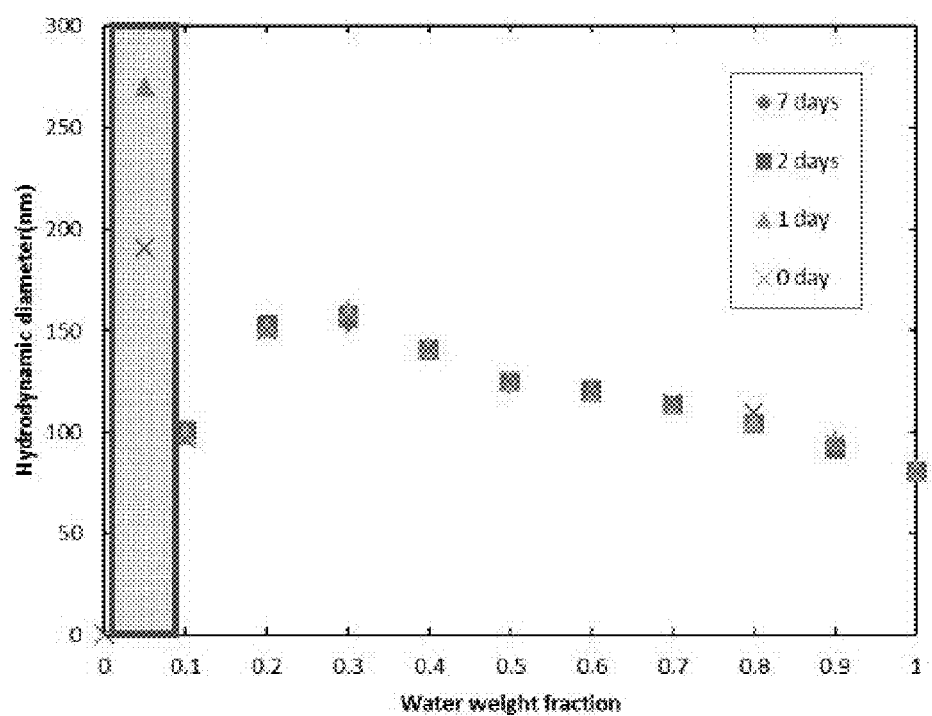
FIG. 6 presents mean hydrodynamic diameters of $PEO_{113}$-$PnBA_{89}$ BCP micelles in a water/DMF mixture, as a function of $w_{water}$ and time. The shaded area represents a solvent composition window in which the BCP molecules aggregate into metastable colloids, signifying a medium for rapid exchange.
Figure 7A:
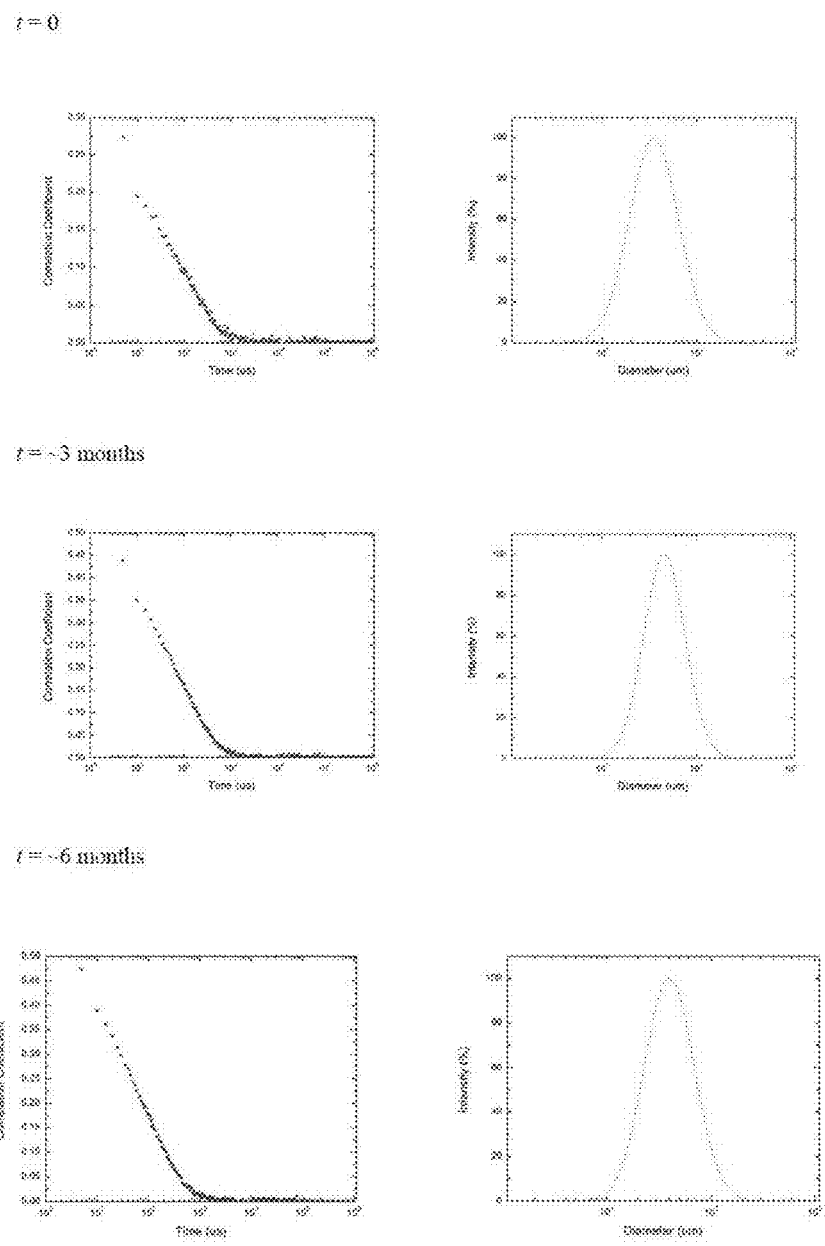
FIG. 7 depicts representative DLS intensity autocorrelation functions and intensity-weighted size distributions (obtained by log-normal analysis) for (FIG. 7A) $PEO_{113}$-$PnBA_{57}$-encapsulated GNRs (prepared by surfactant exchange at $w_{water}$=0.35) in water (DLS data taken at t=0, ~3 and ~6 months after preparation), (FIG. 7B) $PEO_{113}$-$PnBA_{57}$-encapsulated GNRs (prepared by surfactant exchange at $w_{water}$=0.35) in 150-mM NaCl solution (at t=0, ~3 and ~6 months after exposure to 150 mM NaCl), and (FIG. 7C) CTAB-coated GNRs in 150-mM NaCl solution (at t=0, 1 and 2 days after exposure to 150 mM NaCl).
Figure 7B:
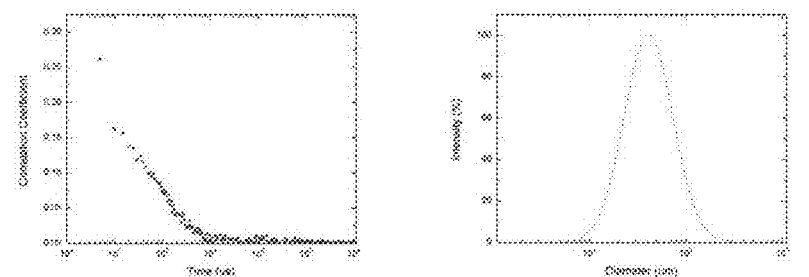
Figure 7B:
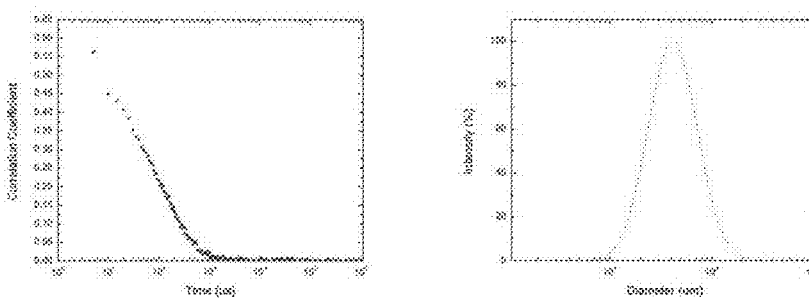
Figure 7B:
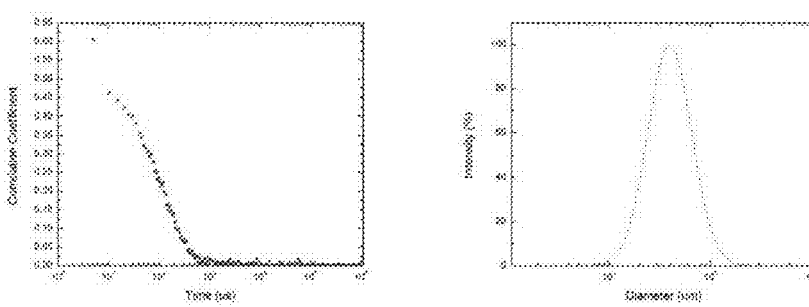
Figure 7C:
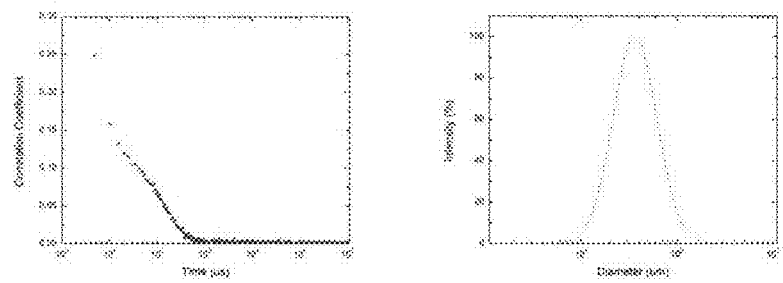
Figure 7C:
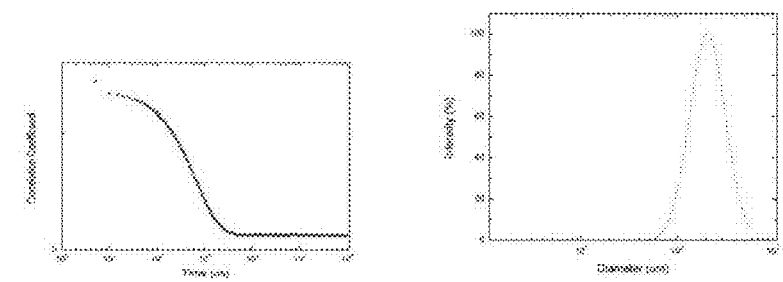
Figure 7C:
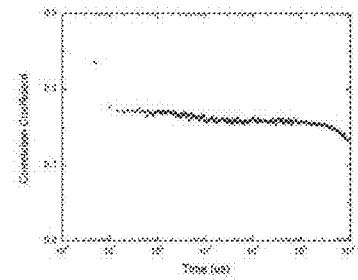

The above result suggests that there exists an optimum window of solvent composition ($w_{water}$ or $1-w_{DMF}$=0.30-0.70) in which the exchange between CTAB and BCP can take place on the surfaces of GNRs. To determine whether the PEO-PnBA polymers are inclined to aggregate into micellar structures in this same solvent composition range, the self-assembly behavior of the PEO-PnBA diblock copolymer $PEO_{113}$-$PnBA_{89}$ as a function of water/DMF weight ratio was investigated. FIG. 6 shows that DMF is a good solvent for both $PEO_{113}$ and $PnBA_{89}$: in pure DMF, the block copolymer is molecularly dissolved and its size is undetectable by dynamic light scattering (DLS).

Figure 3:
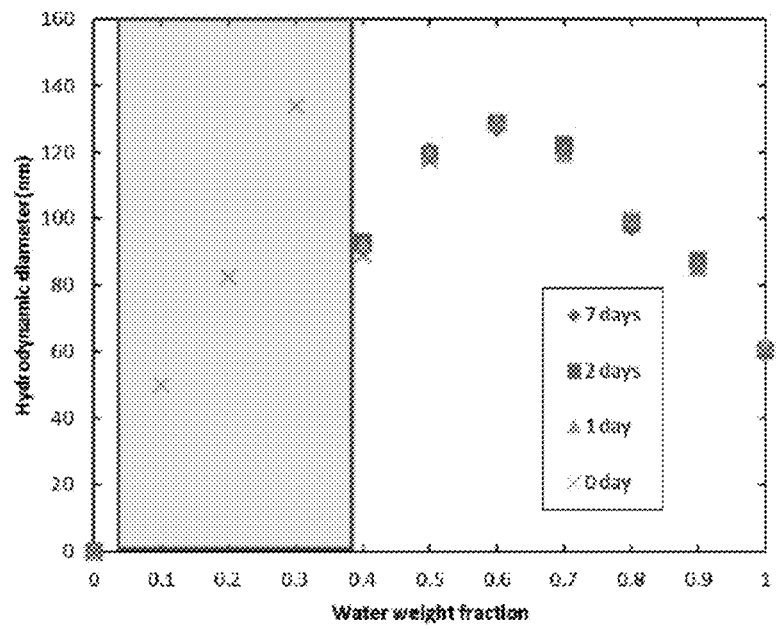
FIG. 3 presents mean hydrodynamic diameters of $PEO_{113}$-$PnBA_{57}$ BCP micelles in a water/DMF mixture, as a function of $w_{water}$ and time. The shaded area represents a solvent composition window in which the BCP molecules aggregate into metastable colloids, signifying a medium for rapid exchange.

The self-assembly behavior of $PEO_{113}$-$PnBA_{57}$, which is more hydrophilic than $PEO_{113}$-$PnBA_{89}$ was studied. The reduced hydrophobic character of the $PnBA_{57}$ segment delayed the onset of kinetic aggregation that occurred during the progressive addition of water into BCP solutions prepared in pure DMF, thereby shifting the window of stable micelle formation to higher values of $w_{water}$. As shown in FIG. 3, when the water fraction was lowered, the metastable BCP clusters were not observed to form until $w_{water}$ ~0.4, permitting an expansion in the solvent composition window for surfactant exchange and GNR encapsulation. This micellization processing window now has a considerable overlap with the solvent window for optimal CTAB exchange (i.e. $w_{water}$ ~0.30-0.40).

Based on the data discussed above, $PEO_{113}$-$PnBA_{57}$ was used and a binary water/DMF solvent mixture with $w_{water}$=0.35, to mediate the exchange and replacement of CTAB on the GNR surface with the BCP layer.

BCP encapsulation trials at several other solvent compositions outside the determined range for optimal CTAB exchange, i.e., at $w_{water}$=0.20 and 0.50 with $PEO_{113}$-$PnBA_{57}$, and also at $w_{water}$=0.05 with $PEO_{113}$-$PnBA_{89}$. The results of these tests failed to produce the desired encapsulation results.

Example 2

Characterization of PEO-PnBA Block Copolymer-Encapsulated Kohl Nanorods

Figure 4:
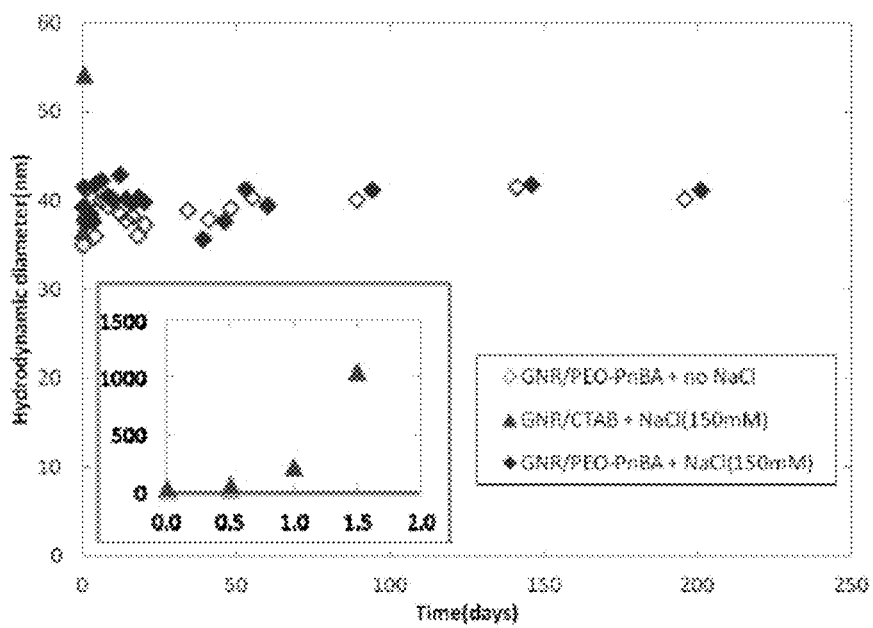
FIG. 4 presents mean hydrodynamic diameters (based on the intensity-weighted size distributions by DLS) of $PEO_{113}$-$PnBA_{57}$ BCP and CTAB-stabilized GNRs in pure water or in 150-mM NaCl solution, as a function of time. The BCP-coated GNRs are stable even at the high ionic strength (■). The CTAB-coated GNRs undergo rapid aggregation at 150 mM NaCl (▲), and the size of the aggregates becomes unmeasurable (>~3 μm) within less than 48 hours. Two data points representing large-sized aggregates formed by the CTAB-coated GNRs were truncated to save space; a plot including all the data points for the CTAB GNR system over a shorter time period is shown in the inset of the figure. Representative DLS correlation functions and intensity-weighted size distributions (obtained by log-normal analysis) for these samples are presented in FIG. 7. The well dispersed nature of the BCP-coated GNR samples and the aggregated nature of the CTAB-coated GNRs have been confirmed also by their respective optical absorbance spectra (data shown in FIG. 8).
Figure 8A:
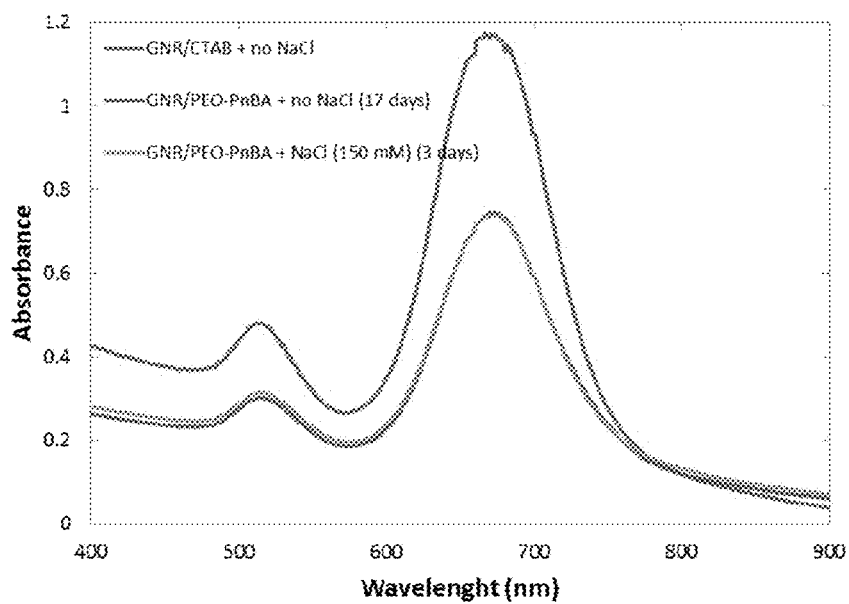
FIG. 8 depicts representative UV-vis absorption spectra (FIG. 8A) for $PEO_{113}$-$PnBA_{57}$-coated GNRs (prepared by surfactant exchange at $w_{water}$=0.35) in water (absorbance data taken at t=17 days after preparation), $PEO_{113}$-$PnBA_{57}$-coated GNRs (prepared by surfactant exchange at $w_{water}$=0.35) in 150-mM NaCl solution (at t=3 days after exposure to 150 mM NaCl), and CTAB-coated GNRs in water (as synthesized), and (FIG. 8B) for CTAB-coated GNRs in 150-mM NaCl solution (at t=0, 1 and 3 days after exposure to 150 mM NaCl).
Figure 8B:
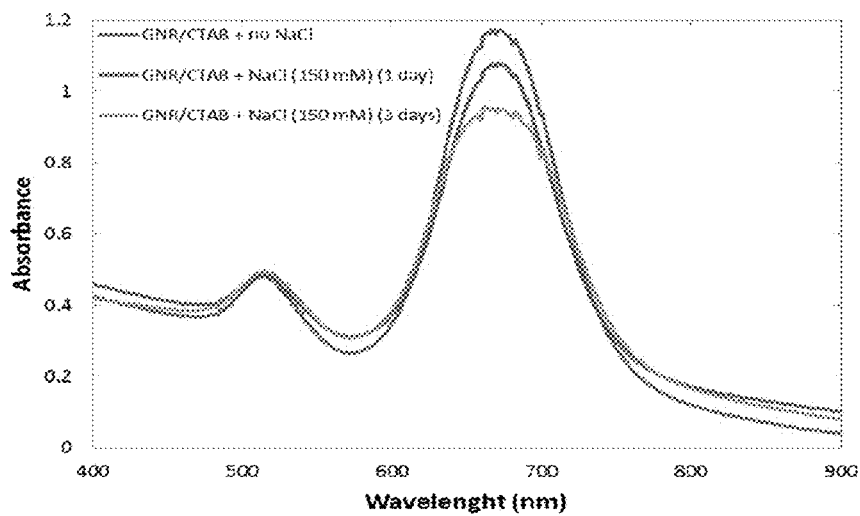
Figure 9:
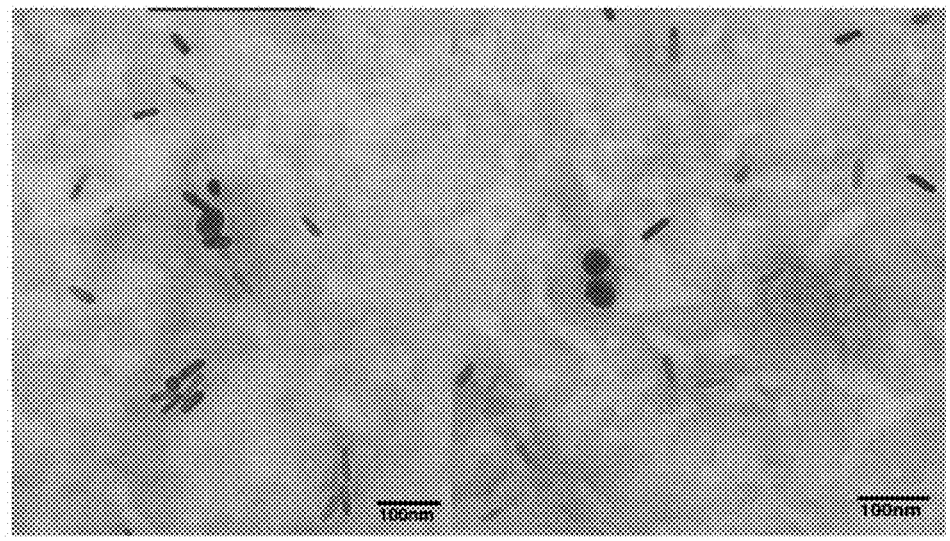
FIG. 9 depicts TEM images of $PEO_{113}$-$PnBA_{57}$ BCP-coated GNRs (prepared by surfactant exchange at a solvent composition of $w_{water}$=0.35) stored in water for 17 days after preparation. The TEM specimens were negatively stained with 2% uranyl acetate. The negative contrast of the polymer layer around an isolated GNR confirms a complete and uniform covering around the GNR particle.
Figure 10A:
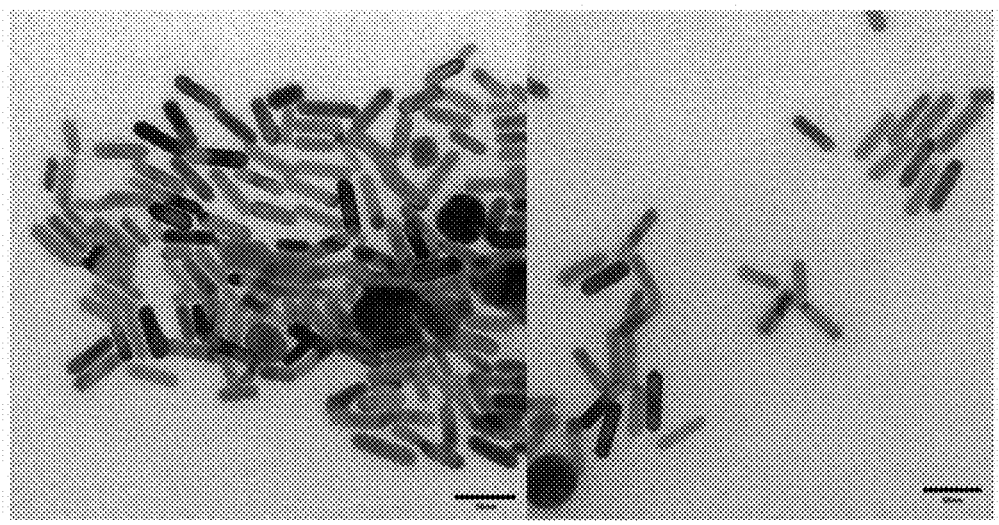
FIG. 10 depicts TEM images of CTAB-coated GNRs (FIG. 10A) as synthesized in water or (FIG. 10B) stored in 150 mM NaCl for 3 days. The TEM specimens were negatively stained with 2% uranyl acetate.
Figure 10B:
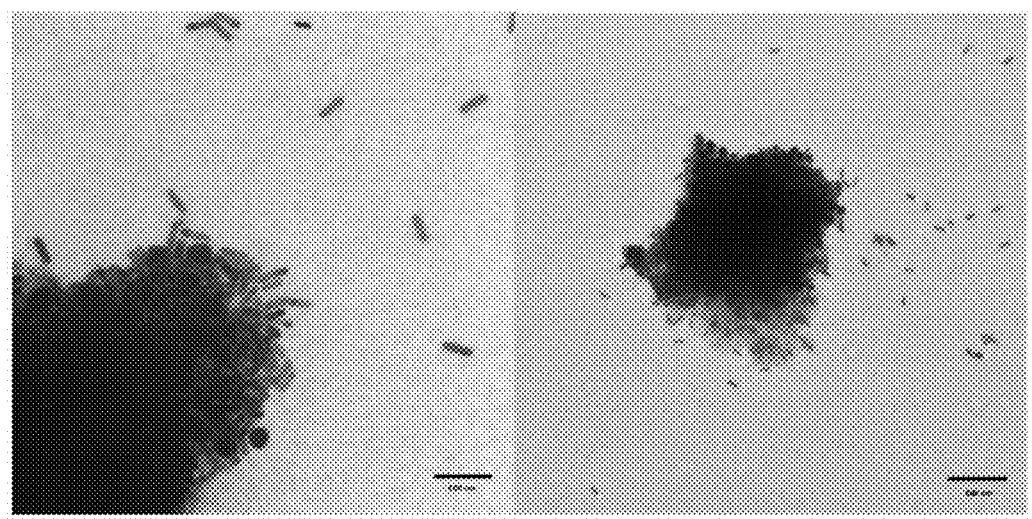

As shown in FIGS. 4 and 8 the effective hydrodynamic diameter of the dialyzed $PEO_{113}$-$PnBA_{57}$-coated GNRs in water was determined to be about 40 nm, which did not change even after almost 7 months of storage. The zeta potential of the BCP-coated GNRs was −1.7±1.1 mV, which suggests that a large (if not all) amount of CTAB has been removed from the GNR surface by the surfactant exchange process (the zeta potential of the original CTAB-coated GNRs was +14.1±0.46 mV).

The stability and hydrodynamic diameter of the BCP-encapsulated GNRs was also monitored by DLS in 150 mM NaCl, over a >6-month period (FIG. 4). This data indicated that the BCP-coated GNRs are stable even at high ionic strength, implying that colloidal stability was derived from entropic steric repulsion provided by the polymer chains of the physisorbed BCP layer. In comparison, CTAB-coated GNRs were unstable under physiological salt conditions and underwent rapid aggregation, because of the screening of the electrostatic double layer provided by the CTAB coating. While some of the CTAB could be replaced or covered by negatively charged polyelectrolytes such as polystyrenesulfonate (PSS), this was insufficient to provide long-term stability to GNR dispersions.

The widely used approach of passivating GNRs with thiol-functionalized PEO did not completely displace the original CTAB coating, with the result being that the PEO-grafted GNRs may not be at least partly inert to protein adsorption in physiological environments. In order to validate the formation of a uniformly dense BCP coating on the GNR surface, transmission electron microscopy (TEM) images were acquired with uranyl acetate staining (see FIG. 5). All GNRs in the TEM images were encapsulated by the BCP micelles (i.e., no uncoated particles were observed), indicating the BCP encapsulation process to be highly efficient. The negative contrast of the PnBA layer around an isolated GNR suggests a complete and uniform covering around the particle with a thickness of 7.3±1.2 nm. From this data, we estimated that each BCP molecule covers an area of 1.4 nm² on the GNR surface, which translates into a normalized area of $\alpha/\pi R_{g,PEO}^2$ ~0.14 per PEO chain, where $\alpha$ denoted the coverage area per PEO chain and $R_{g,PEO}$ was the radius of gyration of the PEO block in the self-avoiding random-walk configuration (~26 Å based on previously reported parameters). Accordingly, the end-grafted PEO chains were extended in a polymer brush configuration ($\alpha/\pi R_{g,PEO}^2 < 1$), and can thus be expected to provide a complete passivation of GNRs against protein adsorption.

Example 3

Structural Properties of Block Copolymer-Stabilized Fe/Au Nanoparticles

Superlattice structure. The pristine Fe/Au nanoparticles were prepared by the Andres aerosol synthesis method. This technique is capable of producing 100-200 mg/h of single or multi-component metal particles with controlled mean diameters ranging from 5-100 nm. The metal or metal mixture of interest was placed inside a tungsten wire basket to which can be resistively heated to 1800° C. The metal atoms evaporated from the tungsten basket and are entrained in a room temperature stream of inert gas. This results in nucleation and rapid growth of solid particles. By controlling the evaporation rate and the flow rate of the inert gas, the mean size of the nanoparticles can be controlled. By controlling the composition of the melt, the atomic composition of bimetallic particles can be controlled. At equilibrium, Fe/Au mixtures phase separate at temperature below about 1000° C. into two crystalline phases. However, because of the rapid cooling provided by the room temperature inert gas, bimetallic particles containing Au and Fe do not phase separate but crystallize as a metastable solid solution. This reactor has been used to synthesize Fe/Au nanoparticles having a 50/50 atomic % of Fe atoms/Au atoms and mean particle diameters of 20-100 nm. It has not yet been determined whether the Fe and Au atoms in the nanoparticles are arranged in an amorphous fashion or in a binary superlattice with a crystalline symmetry. From the magnetic susceptibility value ($\chi \approx 0.12$ emu/Oe g at 298K estimated from the static DC magnetization curve for the Fe/Au (50/50) nanoparticles (FIG. 1), it is approximately estimated that the iron atoms exist in clusters of about ten atoms. The magnetic susceptibility of the Fe/Au particles is at least an order of magnitude higher than the values reported for ordinary iron oxide nanoparticles (i.e., $\chi \approx 0.007$ and 0.004 emu/Oe g for FeO and $\gamma$-$Fe_2O_3$, respectively. Further enhancement of the magnetic susceptibility may be possible by tuning the arrangements of the Fe and Au atoms using various reaction conditions.

Size distribution. As described in the herein above, the size characteristics of the nanoparticles (i.e., the mean size and the size distribution) were controlled during the synthesis process by the evaporation rate and the flow rate of the inert gas. Once produced, these primary nanoparticles were captured by bubbling the aerosol through an aqueous medium containing a temporary stabilizing agent (e.g., sodium carbonate) to form an intermediate nanoparticle suspension. The suspended particles were then encapsulated with the PEO-PnBA BCP via the solvent exchange procedure. Typically, this procedure leads to encapsulation of the nanoparticles in the form of nanoscale agglomerates each containing several primary particles (see FIG. 2). Various processing parameters (e.g., rate of solvent exchange, solvent composition, etc.) influence the final product properties (such as mean size and size distribution). In the magnetic hyperthermia literature, it is well known that the thermal dissipation properties of nanoparticles are significantly influenced not only by the mean size but also by the size distribution of the particles. Therefore, for further optimization of the heat transduction properties of the BCP-stabilized Fe/Au particles, it is necessary to characterize the size distribution characteristics of the particles. The mean particle size data shown in FIG. 2 have been obtained using the dynamic light scattering (DLS) technique. Although the DLS technique is, in theory, also capable of providing information on the size distribution properties, the procedure involves many mathematical assumptions, and therefore the results can only be regarded as an approximate. The precise size distribution characteristics of the BCP-coated Fe/Au nanoparticles are further examined using the analytical ultracentrifugation (AUC) technique.

Example 4

In-Vivo Tumor Accumulation of Block Copolymer-Stabilized Fe/Au Nanoparticles in Mouse Tumor Models Tumor accumulation, biodistribution, pharmacokinetics, and tolerance. The BCP encapsulation method provides a way to render the Fe/Au nanoparticles capable of residing in vivo in the blood compartment. Further, these Fe/Au nanoparticles can also be used as effective MRI contrast agents. The magnetization curve shown in FIG. 11 shows that the particles are superparamagnetic at room temperature with a saturation magnetization of 220 emu/g Fe. This saturation magnetization corresponds to a value of 2.2 unpaired electron spins per Fe atom, and is twice as great as the saturation magnetization of the best system previously known, i.e., the $MnFe_2O_4$ nanoparticles. The $T_1$ and $T_2$ spin relaxation times of water protons in the presence of PEO-encapsulated Fe/Au nanoparticles have been measured using a 3-Tesla MRI system. The spin relaxivities of these Fe/Au particles were found to be dependent on the size of the particles, increasing with particle size; however, typical values measured for 50/50 atomic % Fe/Au particles encapsulated by PEO are $R_1$ (=$1/T_1$)=0.76 and $R_2$ (=$1/T_2$)=189 $(s \cdot mM_{Fe})^{-1}$. These values yield a ratio of $R_2/R_1$=250, which is an order of magnitude higher than has been measured for other magnetic contrast agents. Therefore, this material is an excellent and probably one of the best ever $T_2$ MRI contrast agent. With its capability for microwave-to-heat transduction, this BCP-encapsulated Fe/Au system is, therefore, considered to be a promising nanoparticle platform for theranostic (therapeutic+diagnostic) nanomedicine. Taking advantage of the magnetic properties of the Fe/Au nanoparticles, the in vivo tumor accumulating properties of the BCP-stabilized nanoparticles is characterized using the MRI method.

These in vivo animal experiments are conducted as follows: tumor-bearing mice are used as a model to confirm the accumulation of the nanoparticles in tumors after intravenous (i.v.) administration. Xenograft tumor-bearing mice are prepared by subcutaneously transplanting MDA-MB-231 human breast cancer cells ($10^6$ cells per site) into the flank of athymic nude mice. When tumors reach about 100 $mm^3$, the mice are stratified into three groups (n=6 each) so that the average tumor volume in each group is equal. The tumors are then "treated" (via systemic i.v. delivery) with either saline only (control) or BCP-stabilized Fe/Au nanoparticles. The total amount of the nanoparticles in the body and also the amounts in tumors and other major organs (lungs, bladder, liver, spleen, kidneys and brain) are recorded by MRI. These measurements are conducted at regular intervals over a period of a few days. The mean values of these quantities are calculated for each group, and are compared for statistical significance by Student's t-test and ANOVA. Tumors, as well as major organ samples, are removed at the end of the experiment for quantitative determination of the biodistribution characteristics of the nanoparticles. Tolerance is also determined for each dose by observing appearance and body weight of mice.

The MRI measurements are carried out in a 3-Tesla MRI (GE Signa HDx Imager). Briefly, anaesthetised mice (or excised organ samples) are scanned using an eight-channel, phased-array knee coil simultaneously by placing them next to each other in the center of the coil. A localizer scan is first conducted to sweep the bore of the scanner in all three planes to determine the location of the mice within the scanner. A shorter calibration scan is then conducted to accelerate the subsequent scans' time duration with minimal loss of image quality. Using the images from the localizer, a 3D volume is placed around the mice, centering the mice within the volume. A 3D FSPGR (fast gradient echo pulse sequence), T1-weighted, high-resolution structural scan is then acquired. Finally, three fast spin echo (FSE) scans with varying echo times are performed. The pulse sequence used is a zoomed, coronal FSE, Cube T2-weighted sequence.

Ligand functionalization. BCP-coated Fe/Au nanoparticles are produced which are surface-functionalized with folate ligands as the cell-targeting moiety. The folate receptor is typically overexpressed in breast cancer cells. For this purpose, a folate-functionalized PEO-PnBA BCP is synthesized using the method developed by Won. The same measurements described in the above paragraph are repeated using the folate-functionalized to version of the BCP-encapsulated Fe/Au nanoparticles in order to test whether folate functionalization improves nanoparticle uptake by tumor tissues.

Example 5

Microwave Induction Heating of Block Copolymer-Stabilized Fe/Au Nanoparticles

Theoretical prediction. The microwave absorption spectra of PEG-encapsulated 50/50 atomic % Fe/Au nanoparticles were measured using an electron paramagnetic resonance (EPR) spectrometer. At a microwave frequency of 9.3 GHz, the EPR spectra of a suspension of PEG-encapsulated Fe/Au nanoparticles in DI water was characterized by a large absorption peak at 0.32 Tesla with a full width at half maximum of 0.06 Tesla. This absorption peak corresponds to the spin flip of unpaired electrons in the Fe/Au nanoparticles. From the width of the EPR absorption peak, the life time of the resonant absorption was estimated to be ~$1.8 \times 10^{-10}$ s. Using this data and also the value of ~2.2 unpaired electrons/Fe atom estimated from the measured saturation magnetization (FIG. 11), the thermal power dissipation factor due to the resonant absorption was estimated to be about $8.1 \times 10^5$ kW/g Fe. In a 3-Tesla magnet, the resonant microwave frequency of the Fe/Au particles is 84 GHz, and the estimated power dissipation becomes $7.3 \times 10^6$ kW/g Fe. This estimate of the power dissipation is so much greater than that for any other nanoparticle based scheme for hyperthermal destruction of cancer tumors.

Experiments are conducted using the variable magnet. A microwave cavity designed to measure the temperature rise of a suspension of Fe/Au nanoparticles in water is used to quantitatively determine the power dissipation factor for the resonant excitation of the nanoparticles. Based on this data, experiments are implemented to explore the use of Fe/Au nanoparticles for the in vitro destruction of cancer cells. A microwave generator and cavity tuned to 80-90 GHz so as to be compatible with the 3-Tesla magnetic field of the MRI is also designed and built for study of the in vivo destruction of animal tumors.

Regulatory Approvals

Vertebrate animals (mice tumor models) are used in experiments of this invention. A valid PACUC approval currently exists (Approval #1112000342). Also, an IBC approval on the use of biohazardous materials exists (Approval #12-007).

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A composition of a block copolymer (BCP)-encapsulated metallic nanoparticle, comprising an amphiphilic block copolymer coating and a metallic nanoparticle, wherein the amphiphilic block copolymer coating comprises at least two parts, the first part is a hydrophobic polymer selected from the group consisting of poly(lactic acid) (PLA), poly(lactic acid) (PLA), poly(caprolactone) (PCL), poly(lactic acid-co-glycolic acid) (PLGA) and poly(n-butyl acrylate) (PnBA), and the second part is a hydrophilic polymer, wherein said nanoparticle comprises a metal alloy with two or more metal elements and one of the metal elements is Au, and wherein the block copolymer is configured to interact with the metal alloy through the first part of the block copolymer.

2. The composition of claim 1, wherein said metal alloy further comprises at least one metal element selected from the group consisting of Ag, Pd, Pt, Cu, Cr, Fe, Gd, Mn, and Ni.

3. The composition of claim 1, wherein said nanoparticle comprises Fe/Au.

4. The composition of claim 3, wherein the atomic % of said Au in said Fe/Au nanoparticle is about 50% and wherein the atomic percent of said Fe is about 50% such that the Fe atom/Au atom ratio is about 1:1.

5. The composition of claim 4, wherein said nanoparticle is a superparamagnetic nanoparticle comprising Fe atoms and Au atoms distributed in a solid solution with no observable segregation into Fe-rich or Au-rich phases or regions.

6. The composition of claim 1, wherein said BCP comprises poly(ethylene oxide)-poly(n-butyl acrylate) (PEO-PnBA).

7. The composition of claim 1, wherein said BCP is linked to the surface of said nanoparticle and comprises a hydrophobic part and a hydrophilic part.

8. The composition of claim 7, further comprising a plurality of targeting agents linked to said hydrophilic part.

9. The composition of claim 8, wherein said targeting agents are selected from the group consisting of a nucleic acid, a protein, a peptide, a carbohydrate and a lipid.

10. The composition of claim 1, wherein said BCP comprises poly(ethylene oxide) (PEO).

11. The composition of claim 1, wherein said BCP comprises poly(lactic acid) (PLA).

12. The composition of claim 1, wherein said BCP comprises poly(ethylene oxide) (PEO) and poly(lactic acid) (PLA).

13. The composition of claim 1, wherein said BCP comprises poly(ethylene oxide) (PEO) and poly(caprolactone) (PCL).

14. The composition of claim 1, wherein said BCP comprises poly(ethylene oxide) (PEO) and poly(lactic acid-co-glycolic acid) (PLGA).

15. A composition of a block copolymer (BCP)-encapsulated metallic nanoparticle, wherein said nanoparticle comprises a Fe/Au alloy, and wherein said BCP comprises poly(ethylene oxide)-poly(n-butyl acrylate) (PEO-PnB A).

* * * * *